United States Patent [19]

Boscolo et al.

[11] Patent Number: 4,703,633
[45] Date of Patent: Nov. 3, 1987

[54] AUTOMATIC MACHINE FOR WASHING ARTICLES IN A BATH CONTAINING SURFACTANT SUBSTANCES

[75] Inventors: Antonio Boscolo; Sergio Stibelli, both of Trieste, Italy

[73] Assignee: Zeltron Istituto Zanussi per l'Elettronica S.p.A., Udine, Italy

[21] Appl. No.: 829,094

[22] Filed: Feb. 12, 1986

[30] Foreign Application Priority Data

Feb. 28, 1985 [IT] Italy .............................. 45707 A/85

[51] Int. Cl.$^4$ ...................... D06F 33/02; G01N 15/00
[52] U.S. Cl. .................................. 68/12 R; 73/61 R; 324/61 P
[58] Field of Search ............ 68/12 R, 13 R; 134/113; 324/61 P; 73/61 R

[56] References Cited

U.S. PATENT DOCUMENTS

| | | | |
|---|---|---|---|
| 3,364,812 | 1/1968 | Ewing | 356/339 |
| 3,645,669 | 2/1972 | Rausch | 68/12 R X |
| 4,503,383 | 3/1985 | Agar et al. | 324/61 P |
| 4,510,436 | 4/1985 | Raymond | 324/61 P |

FOREIGN PATENT DOCUMENTS

| | | |
|---|---|---|
| 2854148 | 6/1979 | Fed. Rep. of Germany . |
| 2485576 | 12/1981 | France . |
| 1258839 | 12/1971 | United Kingdom . |
| 2052251 | 1/1981 | United Kingdom . |

Primary Examiner—Philip R. Coe
Attorney, Agent, or Firm—Wenderoth, Lind & Ponack

[57] ABSTRACT

An automatic washing machine for washing articles in a washing bath containing surfactant substances in the form of micelles and/or emulsion includes operative components for controlling the washing operation and a programmable device for controlling the operation of the operative components. At least one device is provided for detecting the microscopic characteristics of the micelles and of the emulsion in the washing bath and for generating signals representative thereof. Such signals are supplied to the control device, such that the control device controls the operation of the operative components in response to such signals.

4 Claims, 6 Drawing Figures

AUTOMATIC MACHINE FOR WASHING ARTICLES IN A BATH CONTAINING SURFACTANT SUBSTANCES

BACKGROUND OF THE INVENTION

The present invention relates to an automatic machine for washing articles, for instance laundry, in a bath containing surfactant substances.

In the case, for instance, of a laundry washing machine, a machine of this type is usually provided with an electromechanical or electronic programming and timing unit, and may also have manually operable means for presetting the various parameters for a washing process to be carried out, such as the amount and type of laundry, the degree of dirtiness, temperature and filling level of the washing solution, etc. All of these devices are associated with the operative components of the machine and permit the user to select a considerable number of washing programs to be carried out by the machine depending on the particular characteristics of the laundry to be cleaned. Each such program may include various phases such as a pre-washing phase, main washing phase, rinsing phase, and centrifuging or spinning phase. Some of these phases may be repeated once or several times for ensuring the best result. After any such program has been suitably selected, it is carried out by the machine in an automatic manner and is terminated after a preselected time which may be different for any given program, the duration of each program having been calculated by the designer of the machine on the basis of laboratory testing procedures.

It is obvious, and in practice it is generally the case, that the operating conditions of the machine in practical use rarely correspond to those assumed by the designer. As a result, any washing cycle may be terminated before the laundry is completely clean, while in other cases the duration of the washing cycle may be longer than actually required. In the first case the result of the washing operation will be unsatisfactory for the user, while in the second case there occurs a waste of energy, water, and detergents.

Various systems have already been devised for avoiding the shortcomings outlined above, but none of these proposals has provided a fully satisfactory solution due to the fact that it is not possible to directly and reliably determine the degree of dirt removal from the laundry.

Known, for instance from British Provisional Patent No. 1,258,839, is the use of a photosensitive device for monitoring the degree of transparency of the water during the rinsing phases and for causing the washing cycle to be terminated when the rinsing water has attained a predetermined degree of clarity. This device cannot, however, ensure complete cleaning of the laundry, as the rinsing water may attain the selected degree of clarity even if certain amounts of dirt still adhere to the laundry. On the other hand, this device does not allow the required amount of detergents, water and energy to be reduced to the indispensable minimum for complete removal of the dirt from the laundry. In other words, this solution only permits a saving of water in the rinsing phases.

From German DE-OS No. 28 54 148, for example, it is also known to employ a sensor disposed within the washing tub for measuring the specific conductivity of the water at successive intervals. The thus determined values are stored and compared to one another. When the difference between two successive values is smaller than a preselected reference value, the rinsing phase is terminated. A similar system is described in French Patent Application No. 2,485,576, employing the use of luminous devices for continually monitoring the degree of purity of the water during the washing and rinsing phases.

From British Patent No. 2,052,251 it is known to control the operation of a laundry washing machine by measuring the surface tension, the hardness, the electric conductivity and the pH value of the water for suitably metering the amounts of water and detergents required for the washing process.

None of the above listed solutions appears fully satisfactory, mainly due to the fact that they are based on the determination of factors which are not truly indicative of the progress of the laundering operation. As a matter of fact, the transparency, the electric conductivity, the hardness and the acidity of the washing bath are scarcely indicative of the actual removal of dirt from the articles to be cleaned. The surface tension, although to a certain degree indicative of the detergent effect of the surfactant substances contained in the detergents supplied to the washing bath, also does not represent totally accurate information. As a matter of fact, the surface tension may be influenced by other variables such as the hardness of the water and the temperature.

SUMMARY OF THE INVENTION

It would therefore be advantageous, and it is a main object of the present invention, to provide an automatic machine for washing articles, adapted to directly monitor the development of the washing process so as to be able to control such process in an optimum manner and to terminate the washing process as soon as the articles have been properly cleaned.

For attaining this object the invention provides a washing machine which is capable of reliably monitoring the progress of the effect of the detergent on the articles introduced into the washing bath. The invention is principally based on the consideration that the removal of contamination or dirt (for instance fatty organic matter) from the articles (for instance fabrics) subjected to a washing process in an aqueous detergent solution is substantially brought about by the absorption of surfactant substances normally contained in detergents by the contamination to thereby reduce the surface tension between the dirty articles and the water. The removal of the dirt is subsequently assisted by mechanical action and by the effect of temperature.

On a microscopic level it is noted in particular that the surfactants usually present in the detergents dissolved in the washing bath are generally composed of hydrocarbon chains agglomerated in the form of micelles and having an apolar hydrophobic end (normally formed by a $-CH_3$ group) and a polar hydrophilic end (for instance of the type $-COOH^-$ or $-SO_3Na^+$). The hydrophobic end of the hydrocarbon chains adheres to the hydrophobic fatty substances, while the hydrophilic end is turned towards the water. During the washing process, the surfactant substances thus solubilize the fatty substances so as to form an emulsion thereof in the washing bath. This results in a corresponding reduction of the number of free detergent molecules for absorption.

The object of the invention thus is attained by the provision of an automatic machine for washing articles in a bath containing surfactant substances in the form of micelles and/or emulsion, such machine including programmable means for controlling the operative components of the machine, at least one device for detecting microscopic characteristics of the micelles and emulsion in the washing bath and for generating signals representative thereof, and adapted to control the control means by such signals.

As a matter of fact, the monitoring of the washing bath at the microscopic level is the only possibility of correctly determining the degree of dirt removal from the articles to be cleaned.

According to another aspect of the invention, the device for detecting the condition of the washing bath preferably comprises electrodes supported on a dielectric substrate and covered by a hydrophobic layer in contact with the washing bath so as to form at least one capacitive element.

BRIEF DESCRIPTION OF THE DRAWINGS

Other objects, features and advantages of the invention will become more clearly apparent from the following description, given by way of example, with reference to the accompanying drawings, wherein.

DETAILED DESCRIPTION OF THE INVENTION

Figure 1:
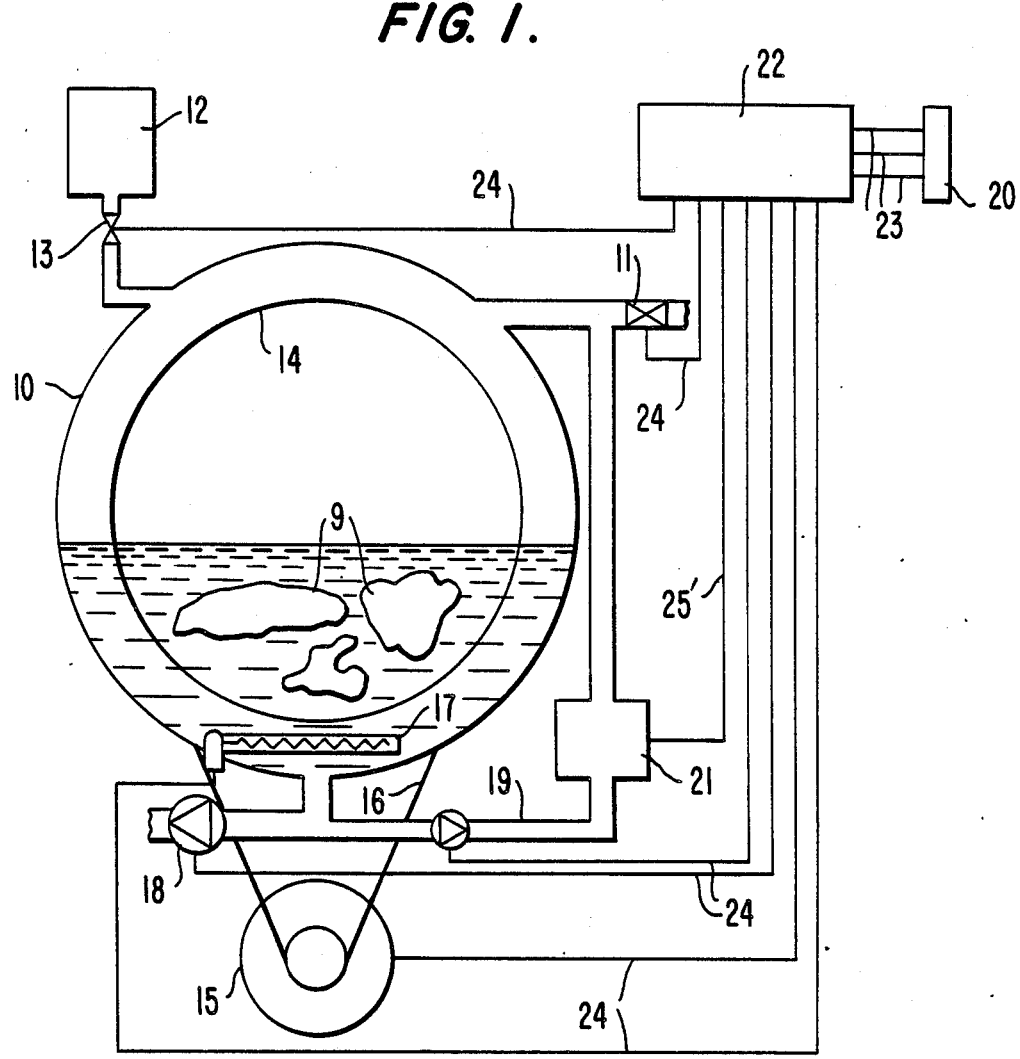
FIG. 1 is a schematic view of an embodiment of the invention in the form of a laundry washing machine.

The laundry washing machine of FIG. 1 comprises a tub 10 adapted to be supplied with water from a main supply through a solenoid valve 11, and with detergent substances, preferably in the form of liquids contained in a reservoir 12 provided with a metering solenoid valve 13. Mounted within tub 10 is a drum 14 for containing the laundry 9 to be laundered. In the per se known manner, drum 14 is adapted to be rotated at different washing and centrifuging speeds by a motor 15 connected thereto through a transmission belt 16. Also mounted in tub 10 is an electric resistance heater 17 for heating the washing liquid, the bottom portion of the tub being connected to a discharge outlet through a pump 18. Connected to tub 10 is a washing liquid recirculation conduit 19 of the type for instance as described in German Utility Model No. 78 13 880.

The laundry washing machine is further provided with selector controls conventionally incorporated in a control panel 20 mounted at a front portion of the machine. These selector controls are connected to respective preset inputs 23 of a programmable control unit 22, preferably of the electronic microprocessor type. Control unit 22 has a plurality of control output terminals 24 for the control of respective operative components of the machine, e.g. elements 11, 13, 15, 16, 17, 18. In addition, control unit 22 is provided with a control input 25'. In a per se known manner control unit 22 (particularly the microprocessor contained therein) is suitably programmed for controlling the operative components of the machine in accordance with the instructions (for instance type and amount of laundry 9) applied thereto by the user by means of control panel 20 and present inputs 23, and with signals applied to control input 25'.

According to the invention, these signals are representative of the microscopic characteristics of the micelles and the emulsion in the washing bath. To this effect, control input 25' is connected to a device 21 for detecting the condition of the washing bath, this device being preferably positioned in the recirculation conduit 19, that is, in a relatively quiescent zone ensuring optimum accuracy of device 21.

Figure 2:
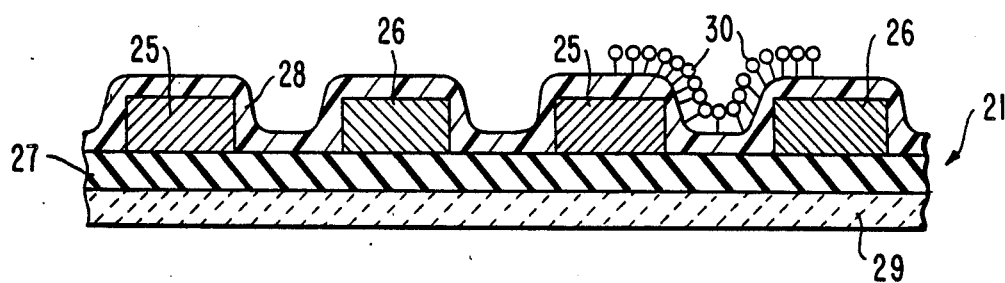
FIG. 2 is an enlarged cross-sectional view of a detail of the machine of FIG. 1.

The detecting device 21 may be of the type described in a patent application by the present inventors, filed concurrently herewith and entitled "APPARATUS FOR MONITORING A WASHING SOLUTION CONTAINING SURFACTANTS" but is preferably of the type shown in FIG. 2. In this embodiment detecting device 21 comprises alternating electrodes 25 and 26 substantially forming a planar electric capacitor. In particular, electrodes 25 and 26 are supported on a dielectric substrate 27 and covered by a thin layer 28 of a hydrophobic substance, for instance a polymer, which is in contact with the washing bath. Dielectric substrate 27 itself is supported on a body 29 of piezo-electric ceramic material adapted to be suitably energized in a per se known manner by control unit 22 for transmitting ultrasonic vibrations to the detecting device 21 as a whole.

Figure 3:
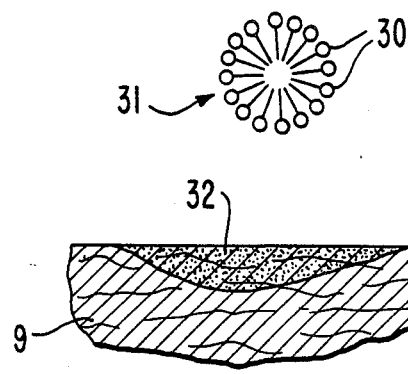
FIGS. 3 to 6 are diagrammatic illustrations, on a microscopic scale, of consecutive phases in the removal of dirt from an article by the effect of surfactant substances.
Figure 4:
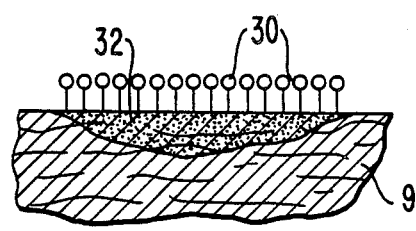
Figure 5:
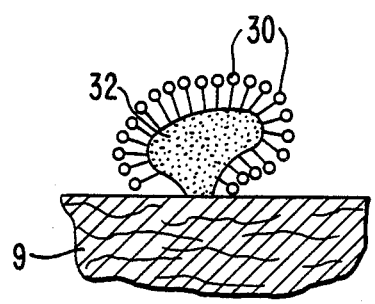
Figure 6:
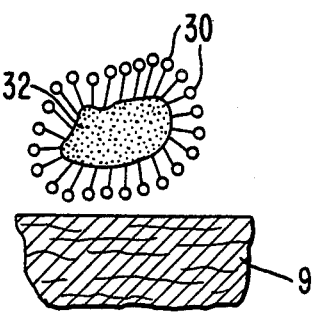

As shown in FIG. 3, the washing bath surrounding laundry 9 after the addition of the detergents contains surfactant substances the molecules 30 of which are agglomerated in the form of micelles 31. The surfactant molecules 30 attach themselves with their hydrophobic ends to a fatty dirt substance 32 (FIG. 4) to release it from the laundry 9 (FIG. 5) and to subsequently form an emulsion (FIG. 6).

In a similar manner, surfactant molecules 30 attach themselves to the hydrophobic covering layer 28 of detecting device 21 (FIG. 2) to thereby alter the capacitive value thereof. This capacitive value has experimentally been found to be proportional to the quantity of molecules 30 attached to layer 28.

In accordance with the programming of the microprocessor, control unit 22 is adapted to energize piezoelectric body 29 at selected intervals to thereby release the attached surfactant molecules from hydrophobic layer 28. In this manner, detecting device 21 is periodically cleaned by means of ultrasonic vibrations, thereby to avoid degradation by smothering of layer 28 and to enable it to determine the variable state of the washing bath at selected intervals.

As already noted, during the progress of the washing operation the surfactant substance solubilizes the fatty substances so as to form an emulsion in the washing bath. As a result, a progressively smaller number of molecules 30 remain free for attachment to layer 28 of detecting device 21, so that the signal applied thereby via input 25' to control unit 22 due to the variation of its capacitive value is indicative of the progressive exhaustion of the detergent and thus of the corresponding variation of the microscopic characteristics of the micelles 31 in the washing bath. In accordance with its basic program, control unit 22 is adapted to control the operative components of the machine in response to the signals applied by signal input 25', thereby to optimize the procedure of washing the laundry 9.

When the degree of absorption of the surfactant substance by detector device 21 remains constant, it is to be concluded that all of the dirt has been removed from the laundry, or that the surfactant substances in the washing bath are exhausted. In the latter case, control unit 22 may be readily programmed by the skilled artisan to cause a further metered amount of detergent to be supplied to tube 10, such detergent, depending on the state of the bath, remaining in free solution or acting to remove further dirt from the laundry 9. As an alternative, it is also possible to raise the temperature of the bath and/or to increase the mechanical agitation thereof. When, under these conditions, the above described state is maintained or regained as revealed by detecting device 21, control unit 22 causes the washing process to be terminated and thus to be optimized.

The washing machine according to the invention is thus capable of effectively operating in a "closed loop" system for optimum cleaning of the articles to be washed. In particular, the machine according to the invention is not programmed simply to carry out the washing process for rigidly predetermined periods of time, but is capable of continuously varying the different factors determining the results of the washing process, such as temperature of the washing bath, mechanical agitation, amounts of water and detergents, in accordance with the state of the washing bath as repeatedly revealed on a microscopic level by the detecting device 21. The advantages achieved in this manner are, on the one hand, an improvement of the result of the washing process, and, on the other, noticeable savings of time, energy consumption, water and detergents.

The described machine may of course be modified in accordance with construction requirements without thereby leaving the purview of the invention. It is thus possible for example to locate detecting device 21 within tub 10 instead of in recirculation conduit 19. Likewise, the machine as a whole may be of a different type other than a domestic laundry washing machine having a rotating drum, for instance a machine for use in industrial installations for washing articles other than fabrics.

Although the present invention has been described and illustrated with respect to preferred features thereof, it is to be understood that other modifications and changes, as would be apparent to one skilled in the art, may be made without departing from the scope of the present invention.

We claim:

1. In an automatic machine for washing dirty articles in a washing bath containing surfactant substances in the form of micelles and/or emulsion, said machine being of the type including operative components, programmable means for controlling the operation of said operative components, sensing means for monitoring the conditions of the washing bath and for generating signals representative thereof, and means for supplying said signals to said control means, such that said control means controls the operation of said operative components in response to said signals, the improvement wherein said sensing means comprises:
   at least one means for detecting the microscopic characteristics of the micelles and of the emulsion in the washing bath, whereby said control means controls the operation of said operative components as a function the actual degree of removal of dirt from the articles being washed.

2. The improvement claimed in claim 1, wherein said detecting means comprises electrodes supported on a dielectric substrate and covered by a hydrophobic layer in contact with a washing bath, and thereby forming at least one capacitive element.

3. The improvement claimed in claim 2, wherein said detecting means further includes ultrasonic generator means for periodically transmitting ultrasonic vibrations to said hydrophobic layer.

4. The improvement claimed in claim 1, wherein said washing bath is contained in a tub provided with at least one recirculation branch conduit, and said detecting means is accommodated in said recirculation conduit.

* * * * *